United States Patent [19]

Bhatia

[11] Patent Number: 5,023,349
[45] Date of Patent: * Jun. 11, 1991

[54] CONTINUOUS PROCESS FOR RAPID CONVERSION OF OLIGOMERS TO CYCLIC ESTERS

[75] Inventor: Kamlesh K. Bhatia, Newark, Del.

[73] Assignee: E. I. Du Pont de Nemours and Company, Wilmington, Del.

[*] Notice: The portion of the term of this patent subsequent to May 30, 2006 has been disclaimed.

[21] Appl. No.: 520,348
[22] Filed: May 8, 1990
[51] Int. Cl.⁵ .......................................... C07D 319/00
[52] U.S. Cl. .................................... 549/274; 549/518
[58] Field of Search ................................ 549/274, 518

[56] References Cited

U.S. PATENT DOCUMENTS 4,727,163 2/1988 Bellis .................................... 549/274
4,835,293 5/1989 Bhatia ................................... 549/274

Primary Examiner—C. Warren Ivy
Assistant Examiner—Ba K. Trinh
Attorney, Agent, or Firm—Charles E. Krukiel

[57] ABSTRACT

A gas-assisted continuous process for the rapid conversion of oligomers of alpha-hydroxycarboxylic acids, esters or salts thereof to cyclic esters in high yields and high states of purity.

12 Claims, No Drawings

CONTINUOUS PROCESS FOR RAPID CONVERSION OF OLIGOMERS TO CYCLIC ESTERS

FIELD OF THE INVENTION

This invention relates to an improved continuous process for preparing cyclic esters by thermolysis of an oligomer of an alpha-hydroxy carboxylic acid, ester or salt thereof at a short residence time. More particularly, the invention relates to a gas-assisted atmospheric pressure process that provides for rapid conversion of the oligomers to cyclic esters, in particular lactide.

BACKGROUND OF THE INVENTION

The preparation of cyclic esters of alpha-hydroxy carboxylic acids is an old and much studied process. Heretofore, the preparation has been conducted in two generally distinct batch steps involving first preparing an oligomer of the hydroxy carboxylic acid, i.e., a relatively short-chain condensation polymer thereof, then heating the polymer under reduced pressure to generate the desired cyclic ester. Grüter et al., U.S. Pat. No. 1,095,205 (1914); Lowe, U.S. Pat. No. 2,668,162 (1954); Bellis, U.S. Pat. No. 4,727,163 (1988); Müller, Ger. Patent Applications 36 32 103 and 37 08 915 (1988). Such processes spanning over 70 years of technology suffer in that they require hours of reaction time at high temperatures for the conversion of the polymeric intermediate to the cyclic ester. Further, the rather long residence times at the high temperatures employed often result in side reactions, leading, for example, to unwanted isomers, charring of the polymer and consequently difficult to handle reactor heels.

It will be noted the Müller German Applications, mentioned above, disclose continuous as well as batch operations for the depolymerization of lactic acid oligomers to lactide where the conversion takes several hours to complete. Müller states his process can be run batchwise, continuously or semicontinuously. These processes, however, depend strongly on greatly reduced pressures for the removal of the desired lactide from the reaction zone. Maintaining such low pressures is not only expensive on a commercial scale but does not solve the problems associated with long residence times. Also, product recovery under vacuum makes downstream processing cumbersome as many of these esters are solid at room temperature. The product obtained has large amounts of impurities, requiring solvent washing and recrystallization; and activated carbon treatment to remove impurities.

It is an object of this invention to provide an improved continuous gas-assisted process at low residence times and at high conversion rates for converting polymers (oligomers) of alpha-hydroxy carboxylic acids or their esters or salts to cyclic esters at high production rates. It is a particular object to provide such a process for producing lactide from the appropriate oligomer of lactic acid, ester of lactic acid or salt of lactic acid.

SUMMARY OF THE INVENTION

A continuous process for preparing a cyclic ester having the formula

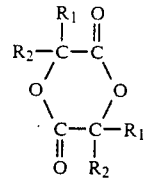

wherein $R_1$ and $R_2$ are independently a hydrogen or an aliphatic hydrocarbyl radical having 1 to 6 carbon atoms, which process comprises (i) continuously feeding an oligomer of an alpha-hydroxy carboxylic acid, $HOCR_1CR_1COOH$, or an ester or a salt thereof, into a reaction zone maintained at a temperature sufficient to liquefy the oligomer and form cyclic ester;

(ii) continuously feeding into the reaction zone a substance that is gaseous and non-reactive at said temperature, said substance forming a gaseous stream contacting the oligomer so as to form a large interfacial area with the oligomer; the amount and flow rate of the gaseous stream within the reaction zone being sufficient for the gas stream to strip cyclic ester from the oligomer substantially as fast as it is formed;

(iii) removing the gas stream containing cyclic ester from the reaction zone; and (iv) recovering the cyclic ester from the gas stream.

In a preferred embodiment the process is carried out at at least atmospheric pressure, as disclosed in Bhatia U.S. Pat. No. 4,835,293.

In another embodiment, the oligomer is fed to the reaction zone, preheated to the reaction temperature.

In another more specific embodiment, the oligomer feed rate and the product stream removal rate are coordinated so as to establish a steady state in that the quantity of reaction mass is maintained substantially constant within the reaction zone.

In particular, the process is directed to the preparation of lactide, including L-lactide, in high yields and high states of purity at high conversion rates, starting with an oligomer of lactic acid or an ester or salt thereof.

This invention is based on the discovery that conversion of an oligomer of an alpha-hydroxy carboxylic acid moiety as defined, such as lactic acid, to a cyclic ester, such as lactide, proceeds more rapidly than heretofore when there is a high interfacial area between the liquid and the gas, and the flow rate of the gas and its volume relative to the amount of oligomer are sufficiently large that cyclic ester is removed substantially as fast as it is formed. Thus, the process is capable of converting lactic acid oligomer, for example, to lactide very rapidly.

Thus, the invention process offers numerous advantages over the art. It substantially reduces the time required for converting an alpha-hydroxy carboxylic-based oligomeric material as defined into the desired cyclic ester. In contrast to the prior processes, which require hours for such conversion, the subject process can produce a cyclic ester such as lactide in much less time. Consequently, the hold-up of reaction mass can be minimized so that loss of potential cyclic ester yield through racemization and charring of the reaction mass can also be minimized. The invention process is therefore capable of producing a cyclic ester such as lactide rapidly and in high yields. Through recycling of unreacted starting material, i.e., unconverted reaction mass, the conversion of cyclic ester can be increased to still higher values.

Further, operating at pressures of about atmospheric reduces investment and operating costs, by eliminating the costly equipment required for maintaining the low reduced pressures utilized in the art. The stripping gas at atmospheric and higher pressures eliminates the potential for explosive atmospheres within the reactor that can result from air leaks, especially at reduced pressures.

DETAILED DESCRIPTION OF THE INVENTION

In general, the process is conducted by continuously introducing an oligomer of an alpha-hydroxy carboxylic acid, an ester thereof or a salt thereof into a reaction zone, preferably preheated to a temperature effective to depolymerize the oligomer to cyclic ester. Substantially simultaneously, a substantially constant flow of a gaseous cyclic stripping agent as defined is passed into the liquid reaction mass in an amount and at a rate so as to create a large interfacial area between the fluid reaction mass and the gas, and the amount of gas is sufficient to strip cyclic ester rapidly from the reaction mass. The stripping gas forms a product stream containing cyclic ester and other volatile material that may be present in the incoming feed stream or reaction mass. The product stream is removed from the reaction zone and the cyclic ester recovered. The cyclic ester may be recovered by any of the methods known to the art, including solvent-scrubbing. One such solvent-scrubbing method is disclosed in Bhatia, U.S. Pat. No. 4,835,293, which disclosure is incorporated herein by reference. Lactic acid and its linear dimer recovered from the reaction product stream in the recovery of the cyclic ester therefrom can be recycled to the reaction zone, either alone or in conjunction with fresh starting material. A purged stream of reaction mass removed from the reactor may also be recycled. It is to be understood that the term "continuous feed" for purposes of this invention comprises both constant and pulsed feeds.

The oligomeric feed material comprises a polymer of an alpha-hydroxy carboxylic acid, ester and/or a salt thereof, viz.,

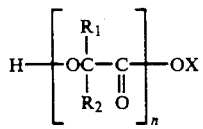

where n is an integer of 2 to 12, X is independently H, $R_3$ or cationic group, $R_1$, $R_2$ and $R_3$ are independently H or a $C_1$-$C_6$ hydrocarbyl radical, and A is a nitrogen base. Preferably, $R_1$, $R_2$ and $R_3$, when other than H in the above formula, is an alkyl group. More preferably, $R_1$ and $R_2$ are H or methyl, as in glycolic acid ($R_1$=$R_2$=H) and lactic acid (R=H, $R_2$=methyl). Preferably, the cationic group is derived from a nitrogen base such as ammonia or alkyl amine. Preferably the nitrogen base is ammonia or an aliphatic amine, preferably a tertiary amine such as trimethylamine, triethylamine, methyldiethylamine, tripropylamine, tributylamine or the like. The molecular weight of the oligomer can vary widely; preferably for the production of lactide it will not be greater than about 1000 for ease of handling. Moreover, the oligomeric polymer should be so constituted, in terms of n, $R_1$, $R_2$, $R_3$ and HA, that it can be liquefied at the operating temperature for depolymerizing it to cyclic ester. Liquidity for purposes of continuously or intermittently feeding the oligomer to the reaction zone can be achieved by preheating the material and/or adding liquidizing quantities, usually minor ones, of a compatible solvent as needed to render the composition conveniently pumpable.

The process of this invention will preferably be conducted in the presence of a catalyst, carried in the feed stream along with the oligomeric reactant or incorporated directly into the reaction mass. The catalyst can be any of those known in the art for promoting the thermolysis of the oligomers to cyclic esters. The catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn (II) carboxylates, especially those that are soluble in the feed stream and the resulting reaction mixture, exemplified by stannous bis(2-ethylhexylcarboxylate), commonly referred to as stannous octoate.

The catalyst will be employed in catalytically effective amounts, which can vary widely depending upon the particular feed material employed and reaction conditions. The optimum catalytically-effective amounts for any particular system can readily be determined through trial runs. For example, with stannous octoate as the catalyst, the quantity will generally be such that the reaction mass contains from about 0.1 to about 1.5% by weight, more usually from about 0.3 to 0.9%.

The reactor may also contain a substantially inert diluent or solvent for the oligomer, such as a high-boiling liquid heat transfer medium, to help minimize localized overheating and charring of the oligomer during its depolymerization to the cyclic ester.

The gaseous agent for entraining/carrying/ sweeping the cyclic ester and water of reaction out of the reaction mixture and out of the reactor may be any substance that is gaseous and stable at the operating temperatures and pressures and is inert to the starting material, reaction mass components and reaction products. It may be normally gaseous, such as nitrogen, argon, carbon monoxide or dioxide or low molecular weight hydrocarbon. It may be normally non-gaseous but gaseous at reaction temperature and pressure. Preferred is $N_2$ for its inertness and ready availability. Preferably, the inert gas will be preheated to or reasonably close to the operating temperature and will be injected below the surface of the reaction mass material in the reaction zone; for example, introduced below the agitator of a stirred tank reactor or fed into the bottom of a vertically disposed reactor so that it can be counter-currently contact down-flowing oligomer. This technique allows one to run a short residence time continuous reaction.

The flow rate of the gas should be sufficiently high so as not to limit the cyclic ester stripping rate. If the flow rate is too low, the conversion to cyclic ester may be adversely affected and its production rate limited since the gas functions importantly to carry the cyclic ester as vapor out of the reactor. The inert gas flow will preferably be at least about 1000 standard cubic feet per minute (scfm) per cubic foot of oligomer fed, more preferably between about 2000 to 5000 scfm per cubic foot of oligomer fed.

Suitably effective temperatures for converting oligomer to cyclic ester can vary widely, but normally will be in the range of from about 185 to 270° C., preferably in the range of from about 200 to 220° C. At these temperatures the resonance times would not be greater than about 45 minutes, preferably not greater than 20 minutes. The optimum temperature for any particular oligomer-to-cyclic ester conversion will vary with composition. For example, for the production of L- or D-lactide the temperature will preferably range from about 190–220° C., for glycolide 220–250° C.

The pressure may vary from sub-atmospheric to atmospheric and super-atmospheric. Preferably it is at atmospheric pressure plus a small back pressure exerted on the product stream equipment which should be designed to keep the back pressure as low as practical, for example, less than 5 psi.

The reactor design and configuration is not critical provided it has means for introducing an oligomer feed stream, means for introducing a gaseous cyclic ester-stripping agent into the reaction zone such that it directly and intimately contacts the oligomeric composition so as to give high gas-liquid interfacial and has means for removing a gaseous stream containing cyclic ester.

Thus the reactor may be a stirred tank equipped with gas-sparging means, preferably one which admits the gas directly under the agitator. The reactor may also be a packed or sieve-plate column, or it may be of any other design known in the art for effecting intimate gas-liquid contact, for example, a spray reactor or a film reactor, again with means for introducing the gaseous component such that it intimately contacts the spray or film of oligomer constituting the reaction mass. Likewise, the product stream recovery and processing system may be any of those known to the art. One such reactor and product recovery system is disclosed in Bhatia U.S. Pat. No. 4,835,293, which disclosure is incorporated herein by reference.

A reactor particularly suitable for depolymerizing oligomeric compositions in accordance with the method of the invention comprises a vertically disposed columnar reactor such as a sieve plate column equipped with means for feeding liquefied oligomer at or near the top of the column, means for removing unconverted liquid reaction mass at the bottom of the column, means for feeding the gaseous component at or near the bottom of the column such that it can pass through the downcoming reaction mass in the column, an exit means at the top of the column for removing the gaseous product stream, and heating means surrounding the column for bringing the reaction mass to the desired temperature and keeping it there.

Oligomeric material to be fed to the reactor should be liquifiable at the operating temperatures. If solid or too viscous to be conveniently fed to the reactor and maintained liquid in the reaction zone, a suitable solvent such as acetone may be used in small quantities sufficient to provide a pumpable fluid mass. Preferably, the feed stream will be preheated to the reaction temperature selected for depolymerizing oligomer to cyclic ester.

The examples that follow are intended to illustrate the invention, and are not to be construed as limiting it to any particular embodiment described herein.

EXAMPLES

Examples 1 and 2 were conducted in a 28 mm Oldershaw distillation column having 5 sieve plates and fitted for the present purpose with an oligomer feed line at the top plate, a fitting for introducing the gas into the column below the bottom-most plate and a gas stream take-off line at the top of the column, a flask for collecting unconverted oligomer from the bottom of the column, and a heating mantle for temperature control. The gas stream line take-off communicated with a scrubbing system for removing cyclic ester from the gas stream. The scrubbing system was described in Bhatia, U.S. Pat. No. 4,835,2933.

EXAMPLE 1

A.

An oligomer of L-lactic acid was prepared by gradually heating a mixture of 754.1 grams of 88% aqueous lactic acid (about 98% L-lactic acid) and 2.54 grams of stannous octoate, over a 2-hour period to 167° C, while removing free water and water of condensation in a small stream of $N_2$ gas. 190 cubic centimeters of aqueous distillate was collected during this period. The reaction mass was held at 160–176° C. for another 0.5 hour, during which time another 6 cc of distillate was collected, and the rate of removal of distillate slowed to essentially nil. The reaction mass was then cooled and mixed with acetone; the resulting composition contained 78.6% oligomer and 21.4%, by weight, acetone, and was sufficiently fluid to be pumped to the reactor at room temperature.

B.

The oligomer-acetone composition from A, having a temperature of just above room temperature, was continuously pumped to the top plate of the 5-plate reactor described above, at a rate of 2.2 gms/min, while a strong stream of $N_2$ gas, preheated to about 185° C., was fed at a rate of 0.14 scfm below the bottommost (5th) plate. The feeds were continued for 2 hours and 15 minutes. The temperature ranged from 186 to 197° C., averaging about 190° C.; the temperature at the 4th plate ranged from 205 to 212° C., most of the time at 210° C.

During the 135 minute run, 305 gms of the feed composition containing 240 gms of oligomer, equivalent to a theoretical 222 gms of lactide, were fed to the column and 86 gms of unreacted oligomer were recovered in the collection flask, corresponding to a conversion of 64%. Reactor hold-up was essentially constant and amounted to about 11 gms. The above data calculate to an inert gas rate of 2750 scfm/cubic foot of oligomer fed. The 97 gms of oligomer (holdup and bottoms) was clear and slightly yellow in color. The residence time of the oligomer in the reactor ranged from about 6 minutes to 17 minutes.

C.

The lactide product was recovered from the $N_2$ gas stream exiting the column by scrubbing with acetone. The acetone solution was partially evaporated under reduced pressures to precipitate a thick lactide. Chilled water was added to further precipitate lactide, which was filtered, the filter cake washed on the filter with isopropyl alcohol and residual solvent removed by evaporating under reduced pressure to yield 86 grams of lactide. An additional 21 grams were recovered from the filtrate and washings, also by concentration under reduced pressure, filtration, washing and drying as before. The 107 grams of white crystalline L-lactide corresponded to 79% of the quantity (136 grams) of oligomer converted.

This product was found to be free of the D-lactide and meso-lactide by high pressure liquid chromatography (HPLC) on a chiral column. Its purity, without recrystallization, was 99.71% by HPLC and 98.69% by differential scanning calorimetry (DSC). It showed a sharp melting point at 97.C as determined by DSC. Upon recrystallization (90% recovery), the purity improved to 99.77% by HPLC and 99.59% by DSC. The melting point was 97.5.C. by DSC. The optical rotation before recrystallization was −288 and after recrystallization from isopropyl alcohol −298., again showing a very high purity.

EXAMPLE 2

The procedure of Example 1 was repeated except that
(a) the oligomer itself, i.e., without added acetone, and preheated to 140° C. to form a liquid feed,
(b) the oligomer feed rate was 1.22 cc/min (1.5 grams/min),
(c) the temperature at the top plate ranged from 204 to 217° C., most of the time was at 215° C.,
(d) the temperature at the fourth plate ranged from 189 to 196° C., most of the time was at 195° C., (e) the inert gas rate was 3300 scfm/cubic foot of oligomer feed rate.
(f) the amount of unconverted oligomer was 13.8 grams, corresponding to a conversion of about 93%.

The lactide product before recrystallization had a purity of 98.5% by HPLC, 99.34% by DSC, and showed a sharp melting point of 98.9.C. Its optical rotation was −294° After recrystallization from isopropyl alcohol, the purity by DSC was 99.69%; and its optical rotation was found to be −300° About 80% of the oligomer converted was recovered from the acetone solution as pure L-lactide product.

What is claimed is:
1. A continuous process for preparing a cyclic ester having the formula

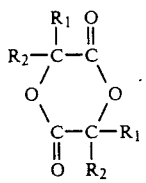

where $R_1$ and $R_2$ are independently a hydrogen or a $C_1$-$C_6$ aliphatic hydrocarbyl radical, which process comprises
  (i) continuously feeding an oligomer of an alpha-hydroxy carboxylic acid, HOCR1R2COOH, or an ester or a salt thereof, into a reaction zone maintained at a temperature effective to liquefy the oligomer and form cyclic ester;
  (ii) continuously feeding into the reaction zone a substance that is gaseous and non-reactive at said temperature, said substance forming a gaseous stream contacting the oligomer so as to form a large interfacial area with the oligomer; the amount and flow rate of the gaseous stream within the reaction zone being sufficient for the gas stream to strip cyclic ester from the oligomer substantially as fast as it is formed;
  (iii) removing the gas stream containing cyclic ester from the reaction zone; and
  (iv) recovering the cyclic ester from the gas stream.

2. The process of claim 1 wherein the reaction zone is maintained at a pressure of at least about atmospheric pressure.

3. The process of claim 2 wherein the pressure is maintained at about atmospheric pressure.

4. The process of claim 2 wherein the oligomer in the reaction zone contains a catalyst effective to depolymerize the oligomer to cyclic ester, the catalyst being present in a catalytically effective amount.

5. The process of claim 4 wherein the catalyst is introduced with the oligomer fed to the reaction zone.

6. The process of claim 2 wherein the temperature is in the range of about 180 to 270° C.

7. The process of claim 6 wherein the temperature is in the range of about 190 to 230° C.

8. The process of claim 3 wherein the oligomer feed is preheated to a temperature at or substantially close to the reaction zone temperature.

9. The process of claim 2 wherein (a) the feed stream is fed at a first rate and the product stream is removed at a second rate, said rates being coordinated and adjusted as necessary to establish a steady state characterized by a substantially constant quantity of reaction mass within the reaction zone, and (b) the feed and product stream rates are maintained to provide substantially constant rate of production of cyclic ester.

10. A process according to any of the above claims wherein the oligomer is an oligomer of lactic acid and the cyclic ester product is lactide.

11. The process of claim 10 wherein the oligomer is an oligomer of L-lactic acid and the cyclic ester product is L-lactide.

12. The process of claim 10 wherein the oligomer is D-lactic acid and the cyclic ester product is D-lactide.

* * * * *